United States Patent [19]
David et al.

[11] Patent Number: 4,959,459
[45] Date of Patent: Sep. 25, 1990

[54] SURFACE ACTIVE COMPOUNDS AND A PROCESS FOR THEIR PREPARATION

[75] Inventors: Marie-Henriette L. David, Gent, Belgium; Horst Guenther, Willich, Fed. Rep. of Germany; Hilde O. J. Lemmens, Hoboken; Harald W. W. Roeper, Brussels, both of Belgium

[73] Assignee: Cerestar Holding BV, Sas Van Gent, Netherlands

[21] Appl. No.: 325,525

[22] Filed: Mar. 20, 1989

[30] Foreign Application Priority Data

Mar. 21, 1988 [GB] United Kingdom ................ 8806691

[51] Int. Cl.$^5$ ........................ C07H 1/00; C07H 3/00; C08B 37/00; C07G 3/00
[52] U.S. Cl. ..................................... 536/1.1; 536/4.1; 536/18.5; 536/124; 435/74; 435/913; 435/921; 435/931; 435/939
[58] Field of Search ........................ 536/1.1, 4.1, 18.5, 536/124; 435/74, 913, 921, 931, 939

[56] References Cited

U.S. PATENT DOCUMENTS

| | | | |
|---|---|---|---|
| 2,759,922 | 8/1956 | Gibbons | 536/18.2 |
| 2,759,923 | 8/1956 | Gibbons | 536/18.2 |
| 2,931,797 | 4/1960 | Gibbons et al. | 536/18.2 |
| 4,614,718 | 9/1986 | Seino et al. | 435/72 |
| 4,687,843 | 8/1987 | Smolin et al. | 536/18.3 |
| 4,716,152 | 12/1987 | Kruger et al. | 536/4.1 |

FOREIGN PATENT DOCUMENTS

| | | |
|---|---|---|
| 0144894 | 6/1985 | European Pat. Off. |
| 3430944 | 3/1985 | Fed. Rep. of Germany |
| 60-26831 | 8/1986 | Japan |
| 62-195292 | 8/1987 | Japan |
| 63-112993 | 5/1988 | Japan |
| 1392779 | 9/1973 | United Kingdom |
| WO8605186 | 2/1986 | World Int. Prop. O. |
| WO8901480 | 8/1988 | World Int. Prop. O. |

OTHER PUBLICATIONS

16–Fermentations, p. 533, vol. 105, 1986.
JAOCS, vol. 61, No. 11, pp. 1761-1765—Enzymatic Synthesis of Carbohydrate Esters of Fatty Acid(1) Esterification of Sucrose, Glucose, Fructose and Sorbitol.
J. Am. Chem. Soc. 1986, 108, 5638-5640.

*Primary Examiner*—Nathan M. Nutter
*Attorney, Agent, or Firm*—Cushman, Darby & Cushman

[57] ABSTRACT

6-$C_8$ to $C_{22}$ acyl-1-$C_3$ to $C_{12}$ alkylglucosides are a new group of surface active compounds useful in particular as emulsifiers in cosmetics, pharmaceutical compositions and foodstuffs. They are prepared by reacting a 1-$C_3$ to $C_{12}$ alkyl glucoside with a $C_8$ to $C_{22}$ fatty acid in the presence of a lipolytic enzyme and in a reaction medium containing at most 30% and preferably 0.01 to 5% water.

17 Claims, No Drawings

SURFACE ACTIVE COMPOUNDS AND A PROCESS FOR THEIR PREPARATION

The present invention relates to a novel group of surface active compounds and to a process for their preparation.

European patent application No. 1448894 (equivalent to U.S. Pat. No. 4716152) describes a large group of compounds having the general formula

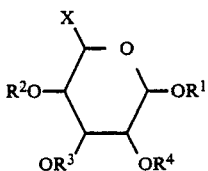

in which
X is hydrogen or the radical $CH_2OR^5$,
$R^2$, $R^3$, $R^4$ and $R^5$ each independently is hydrogen or the radical

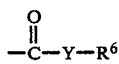

Y is oxygen, sulphur, NH or $CH_2$, and $R^1$ and $R^6$ each independently is an optionally substituted hydrocarbon radical having up to 50 carbon atoms provided that at least one of $R^1$ and $R^6$ contains between 9 and 50 carbon atoms. This group of compounds is described as having pharmaceutical properties and as being useful in the stimulation of the immune system of a patient.

Offenlegungsschrift 3430944 describes a process for the preparation of fatty acid esters of sugars and sugar alcohols which esters find use in the foodstuffs industry as non-ionic surface active agents. The Offenlegungsschrift describes the problems encountered in preparing such esters by standard esterification techniques mainly because of the high temperatures involved which cause discolouration in the products. In order to avoid these problems a process is described in the Offenlegungsschrift in which an aqueous mixture of a $C_8$ to $C_{22}$ fatty acid and a sugar or sugar alcohol is incubated with a lipolytic enzyme at a temperature of about 20° to 60° C. and the desired ester separated from the mixture.

We have found that the process as described in 3 430 944 is difficult to operate successfully because, we believe, solubility factors in the aqueous environment are unfavourable for the sugar and sugar alcohol molecules to adopt a configuration suitable for the action of the lipolytic enzyme and because the aqueous environment favours the reverse reaction i.e.. the hydrolysis of the desired sugar or sugar alcohol ester.

A recently published Japanese patent application J62195-292-A describes a modification of the process of the German Offenlegungsschrift in which the initial aqueous system is incubated under reduced pressure so that water is gradually removed. When the water content reaches less than 5% the incubation is continued under normal pressure. Although this process attempts to improve the process of DT-OS 3430 944 it is our experience that yields are still low when sugars or sugar alcohols recommended in the Japanese application i.e. glucose, sucrose, raffinose, dextrin, mannan, cellulose, sorbitol, xylitol, are used in the process to produce the desired fatty acid ester surface active agents.

Another Japanese patent application 63-112993 published on the 18th May 1988 describes a process in which the sugar or sugar alcohol is made lipophilic by acetylation and the reaction with the fatty acid which is catalysed by the lipolytic enzyme is then carried out in an organic solvent.

Fatty acid esters of sugars and sugar alcohols are commercially attractive products so there is a considerable incentive, as shown by the German and Japanese patent applications referred to above, to produce them or their equivalents by an economic and viable process.

We have now found a group of modified sugar esters which may be produced by esterification of the modified sugar with a fatty acid in the presence of a lipolytic enzyme in high yield and of good quality and which possess surface active properties at least equivalent to the fatty acid esters of the unmodified sugars and sugar alcohols.

Accordingly, the invention comprises a novel group of surface active compounds which are
6-$C_8$ to $C_{22}$ acyl-1-$C_3$ to $C_{12}$ alkylglucosides.

The invention also comprises a process for the preparation of the novel compounds in which a 1-$C_3$ to $C_{12}$ alkyl glucoside is contacted with a $C_8$ to $C_{22}$ fatty acid in the presence of a lipolytic enzyme in a reaction medium containing at most 30% by weight water based on the total weight of the reaction medium.

In U.S. Pat. No. 2 759 922 there is described a process for making fatty acid esters of methyl and ethyl glucosides by heating the glucoside with the fatty acid at 160° to 300° C. The use of such lower alkyl glucosides in our process is however ineffective while the product of the process of U.S. Pat. No. 2 759 922 tends to be a mixture of esters in which, as well as at the 6-position, reaction takes place at other positions in the glucose molecule. In the process of the present invention on the contrary the 6-derivative is effectively the only product.

The process of the invention is suitable for use with 1-alkylglucosides in which the alkyl group contains 3 to 12 carbon atoms, preferably 4 to 8 carbon atoms, the butyl glucosides, especially the n-butyl derivative being particularly effective. The process is not however applicable to sugars in general and disaccharides such as sucrose are not suitable nor are sugar alcohols. Thus, sorbitol, the sugar alcohol derived from glucose, is ineffective in the process of the invention.

The fatty acids which provide the acyl group in the novel compounds of the present invention may have 8 to 22 carbon atoms and preferably have 10 to 20 carbon atoms. Fatty acids having less than 8 carbon atoms give very poor Yields if they are used in the process. Specific examples of fatty acids which may be used in the process of the invention are capric acid, lauric acid, myristic acid, oleic acid, linoleic acid or arachidic acid. Mixtures of fatty acids may also be used e.g. commercially available mixtures such as those derived from coco, corn, cottonseed, linseed and soya.

The source of the lipolytic enzyme for use in the process of the invention is unimportant and lipolytic enzymes from yeasts or of animal, vegetable, bacterial or fungal origin may be used. Thus, lipolytic enzymes from wheat germ, pig pancreas, Aspergillus sp., Mucor sp., Rhizopus sp. and Candida cylindraceae are all suitable for the production of the novel compounds according to the present invention.

Although the process of the invention may be carried out in a reaction medium containing up to 30% by weight of water it is preferred that the water content of the reaction medium be less than 15% by weight and most preferred operation takes place at water contents in the range 0.01 to 5% by weight of the reaction medium.

The temperature at which the process of the invention is operated may be 20° to 60° C. preferably 25° to 50° C.

The reaction medium may be composed of the alkylglucoside and the fatty acid or an inert solvent may also be present, particularly an inert hydrophobic solvent e.g. a paraffinic solvent such as hexane. The molar ratio of the alkylglucoside to fatty acid may lie in the range 0.001 to 5:1 preferably 0.1 to 2:1. The amount of lipolytic enzyme which may be used in the process depends upon the purity and activity of the enzyme in question. If the activity of 0.05 mg of commercially available lipolytic enzyme of Candida cylindraceae is equivalent to 1 unit/gram of glucoside plus fatty acid the preferred range of concentration of enzyme in the process is that required to provide 25 to 100 units/gram glucoside plus fatty acid. The activity of a sample of lipolytic enzyme is determined by the method described by N. W. Tietz and E. A. Fiereck "Measurement of lipase in serum" Standard Methods of Clinical Chemistry, G.R. Cooper, Editor, New York Academic Press, 1972, Vol. 7, pp. 19–31.

The process of the invention may be carried out batchwise or continuously. Effective continuous operation may be achieved by using the lipolytic enzyme held on or in an inert support such as silica or a synthetic resin such as a phenol/formaldehyde resin.

The novel products of the invention are excellent surface active agents which have applications in a wide range of industries. Their surface active activity may be varied by varying in particular the chain length of the fatty acid used to esterify the alkylglucoside but also by varying the chain length of the alkyl group in the alkyl glucoside itself. They find applications as emulsifiers in cosmetics, pharmaceutical compositions and foodstuffs and may be used in compositions in amounts which are conventional for this type of product e.g. 1 to 10% by weight.

The invention will now be further described with reference to the following Examples.

Comparative Example A

Reaction of oleic acid with 1-methylglucoside 1 gram of a commercially available lipolytic enzyme of Candida cylindraceae was dissolved in 60 mls water at pH 6.0. Silica gel 60 (MN) (3.0 gram) was then added to the enzyme solution followed by 90 mls acetone added in drops over a period of 30 minutes, the solution temperature being maintained at 10° C. After separation from the solution by filtration the silica gel was washed with 50 mls of chilled acetone to displace residual water. Approximately 0.1 gram of lipolytic enzyme was immobilised per gram silica.

50 grams Methylglucoside (25 grams alpha-methyl glucoside and 25 grams beta-methylglucoside) were dissolved in 21.7 grams water at 70° C. The solution was then cooled to ambient temperature and 145.21 grams oleic acid and 3.8 grams of the immobilised enzyme added. The mixture was stirred at 1000 rpm at ambient temperature for 216 hours.

The progress of the reaction was followed by thin-layer chromatography but only traces of the 6-oleic acid ester of 1-methylglucoside were formed.

EXAMPLE 1

7 grams of 1-n-butylglucoside (72% dry substance) were mixed with 11.9 grams oleic acid and 0.33 gram of the immobilised lipolytic enzyme of Candida cylindraceae added to the mixture.

The mixture was stirred at 500 rpm at ambient temperature for 96 hours, the reaction being followed by thin-layer chromatography and gel-permeation chromatography. 5.7 grams of the 6-oleic acid ester of 1-n-butylglucoside were formed.

Comparative Examples B, C and D

Comparative Example B 4.27 grams sucrose were dissolved in 250 mls aqueous phosphate buffer solution (0.1 molar pH 5.4) and 14.1 grams oleic acid and 0.5 gram Candida cylindraceae lipolytic enzyme added to the solution. The solution was then stirred at 1000 rpm and 40° C. for 72 hours after which time the whole reaction mixture was freeze dried and extracted with chloroform (soxhlet extraction). The choroform was next removed by vacuum evaporation and the residue dissolved in tetrahydrofuran and analysed by thin-layer chromatography and gelpermeation chromatography. No oleic acid ester was detected.

Comparative Example C

Replacement of the sucrose in Example B by the equivalent amount of sorbitol did not produce the oleic acid ester of sorbitol.

Comparative Example D

Examples B and C were repeated but increasing the enzyme present fivefold. No oleic acid esters were detected.

Example 2

Reaction of oleic acid with 1-n-octylglucoside 1 gram of 1-n-octylglucoside dissolved in 1 ml water was mixed with 5 mls oleic acid and 5 mls n-hexane. 20 mg. Candida cylindraceae lipolytic enzyme as then added and the mixture stirred at 1000 rpm at ambient temperature for 120 hours. The yield of product was determined by thin-layer chromatography and by gel permeation chromatography and was found to be 0.5 gram of the 6-oleic acid ester of 1-n-octylglucoside.

EXAMPLE 3

Preparation of 6-oleyl-1-n-butylglucoside 407 grams of n-butylglucoside (70% dry substance) were mixed with 339 grams oleic acid, 1.6 grams of the lipolytic enzyme from Candida cylindraceae added and the mixture stirred at ambient temperature for 24 hours. Residual oleic acid was next removed by extraction with n-hexane and n-butylglucoside and 6-oleyl-1-n-butylglucoside separated chromatographically using two columns in series which were packed with silica, the eluant being a 90/10 mixture of chloroform and methanol at a flow rate of 100 ml/min.

The eluant was finally removed by distillation leaving 140 grams of 6-oleyl-1-n-butylglucoside of 99% purity.

EXAMPLE 4

Preparation of 6-lauryl-1-n-butylglucoside 212 grams of n-butylglucoside (70% dry substance) were mixed with 252 grams lauric acid which had been liquified by heating at 50° C. 1 gram of the lipolytic enzyme of Candida cylindraceae was then added to the mixture which was stirred at 200 rpm at 50° C. for 24 hours.

The 6-lauryl-1-n-butylglucoside was recovered from the reaction medium by:
(a) stepwise extraction of the residual lauric acid with n-hexane, the removal being monitored by gel-permeation chromatography, followed by,
(b) addition of water which resulted in the solution of n-butylglucoside the 6-lauryl-1-n-butylglucoside separating as an oily upper phase.

The yield was 100 grams of 6-lauryl-1-n-butylglucoside of 80% purity.

We claim:

1. A group of surface active compounds which are 6–$C_8$ to $C_{22}$ acyl-1-$C_3$ to $C_{12}$ alkylglucosides.

2. A process for the preparation of a 6–$C_8$ to $C_{22}$ acyl-1-$C_3$ to $C_{12}$ alkylglycoside comprising the steps of:
(a) contacting a 1–$C_3$ to $C_{12}$ alkylglucoside with a lipolytic enzyme in a reaction medium, the reaction medium comprising a $C_8$ to $C_{22}$ fatty acid and 0.01 to 30% by weight water;
(b) agitating the mixture from step (a); and
(c) separating out 6-$C_8$, to $C_{22}$ acyl-1-$C_3$ to $C_{12}$ alkylglucoside.

3. Compounds according to claim 1 in which the 1-$C_3$ to $C_{12}$ alkyl glucoside is a butyl group.

4. Compounds according to claim 1 or clam 3 in which the fatty acid is a $C_{10}$ to $C_{20}$ fatty acid.

5. A process according to claim 2 in which the lipolytic enzyme is derived from Aspergillus sp., Mucor sp., Rhizopus sp., Candida cylindraceae, pig pancreas or wheat germ.

6. A process according to claim 2 in which the lipolytic enzyme is immobilised on an inert support.

7. A process according to claim 2 in which the process is carried out in an inert solvent.

8. A process according to claim 2 in which the temperature is 25 to 50° C.

9. A process according to claim 2 in which the molar ratio of 1-$C_3$ to $C_{12}$ alkylglucoside to the fatty acid is in the range 0.001 to 5 to 1.

10. A process according to claim 2 in which the amount of water present is 0.01 to 5% by weight of the reaction medium.

11. A cosmetic composition comprising 1 to 10% the surface active compound 6-$C_8$ to $C_{22}$ acyl-1-$C_3$ to $C_{12}$ alkylglucoside according to claim 1.

12. Compounds according to claim 4 in which the $C_{10}$ to $C_{20}$ fatty acid is capric acid, lauric acid, myristic acid, oleic acid, linoleic acid or arachidic acid or a commercially-available mixture of fatty acids.

13. A process according to claim 2 in which the glucoside is 1-butyl glucoside.

14. A process according to claim 2 in which the fatty acid is a $C_{10}$ to $C_{20}$ fatty acid.

15. A process according to claim 14 in which the fatty acid is capric acid, lauric acid, myristic acid, oleic acid, linoleic acid or arachidic acid or a commercially-available mixture of fatty acids.

16. A pharmaceutical composition comprising 1 to 10% of the surface active compound 6-$C_8$ to $C_{22}$ acyl-1-$C_3$ to $C_{12}$ alkylglucoside according to claim 1.

17. A foodstuff comprising 1 to 10% of the surface active compound 6-$C_8$ to $C_{22}$ acyl-1-$C_3$ to $C_{12}$ alkylglucoside according to claim 1.

* * * * *